(12) United States Patent
Pera

(10) Patent No.: US 8,198,097 B1
(45) Date of Patent: Jun. 12, 2012

(54) FREE RADICALS URINE TEST KIT FOR USE IN THE HOME

(76) Inventor: Ivo E. Pera, Pembroke Pines, FL (US)

( * ) Notice: Subject to any disclaimer, the term of this patent is extended or adjusted under 35 U.S.C. 154(b) by 1207 days.

(21) Appl. No.: 11/859,003

(22) Filed: Sep. 21, 2007

(51) Int. Cl.
*G01N 33/00* (2006.01)
*G01N 21/03* (2006.01)

(52) U.S. Cl. .......................................... 436/128; 436/165

(58) Field of Classification Search .................. None
See application file for complete search history.

(56) References Cited

U.S. PATENT DOCUMENTS

| 6,835,554 | B2 * | 12/2004 | Glagau et al. | 435/25 |
| 7,514,265 | B2 * | 4/2009 | Yoon et al. | 436/128 |
| 2003/0203495 | A1 * | 10/2003 | Rupp | 436/74 |

OTHER PUBLICATIONS

Edda B. Hoving et al."Optimized determination of malondialdehyde in plasma lipid extracts using 1,3-diethyl-2-thiobarbituric acid: influence of detection method and relations with lipids and fatty acids in plasma from healthy adults", 1992, Clinica Chimica Acta, vol. 208, 63-76.*

* cited by examiner

*Primary Examiner* — Blaine Lankford, Jr.
*Assistant Examiner* — Charles Z Constantine
(74) *Attorney, Agent, or Firm* — Daniel S. Polley, P.A.

(57) ABSTRACT

A do-it yourself test kit as a diagnostic agent for the detection of malonyldiadeyde and other aldehydes in the urine, which are formed in the course of the lipid peroxidation process caused by the free radicals. Also disclosed is a process for the preparation of the test, including suggested formulations of antioxidants as body's protectors against oxidative stress to the cells and help to reduce the risk of developing diseases due to the attack of free radicals.

18 Claims, No Drawings

FREE RADICALS URINE TEST KIT FOR USE IN THE HOME

FIELD OF THE INVENTION

The present invention relates generally to urine test kits and particularly to a composition and method of making a do-it yourself free radicals urine test kit for the assessment of oxidative stress by colormetric analysis. The invention also provides suggested formulations to use antioxidants to protect the body against toxic damage caused by free radicals.

BACKGROUND OF THE INVENTION

The formation of urine and its excretion are critical physiological activities of the body, which provide a mechanism for the maintenance of a constant internal environment for all cells, tissues and organs. This internal ecology of the body is well recognized and is known as homeostasis. In as much as the urine reflects what is occurring within the body, it offers a fluid, which is an important source of information that is most useful as an aid in the definition of states of health and disease.

Urine is quite widely studied as a means of identifying abnormalities associated with disease. The importance of such study is emphasized by the fact that the number of tests carried out on urine far exceeds those made on all other body fluids combined.

Superoxide and hydroxyl radicals are the more common radicals centred on oxygen, both generated from molecular oxygen under reducing conditions. In particular, superoxide anion is produced as by-product (1-2%) in the ATP biosynthesis by mitochondria. Due to the radicals formation in the metabolic pathways, living organisms have developed mechanisms for minimizing damages caused by undesired reactions of these intermediates.

Free radicals, especially those centered on oxygen, are not easily detectable because of their reactivity. Some of them have high reactivity. Some of their metabolites, e.g. hydroperoxides, can be detected.

A possible metabolic pathway for free radicals involves the reaction with unsaturated esters to give lipidic radicals and finally lipidic peroxides; further transformations of these intermediates give a certain amount of metabolites that can be revealed in human plasma and/or urine.

Among these final metabolic products (markers) the more extensively studied are:
a. Malondialdehyde (MDA): it is present at concentration of 1 uM in human plasma and 0-3 uM (0-02 ppm) in urine.
b. Isoprostans: structurally derived from prostaglandins but they come from a completely different metabolic pathway; it is likely that free radicals play a fundamental role in the production of isoprostans, therefore they are taken as very useful markers in the non-invasive assessment of oxidative stress in mammals. The 8-isoprostan is present in small amounts (10-20 ppt) in plasma and in higher amounts (0.5-3 ppb) in human urine.
c. 3-Nitro-tyrosine: produced from free radicals in the type NO; it seems a promising marker for the assessment of the oxidative stress. Urine concentrations are however quite low (0-8 ppb).

The human body to defend itself has developed numerous physical processes by which some result is produced. In order to scavenge free radicals the body uses antioxidants, but depending on life style and environmental conditions, often depending on life style and environmental conditions antioxidants are not available in sufficient quantities to neutralize the free radicals, therefore neutraceutical supplements are needed.

The ready availability of urine is an advantage that makes it practical as a material for monitoring the course of treatment of disease as well as for its recognition and definition.

MDA is the most widely used marker for oxidative stress. Different analytical method allow the determination of MDA in biological fluids; among them, the following are worth to mention: the Schiff reagent (Pararosaniline sulphate); indolic derivatives; the Thio-Barbituric acid (TBA).

The detection of Malonyldialdehyde and other Aldehydes in the blood and/or urine has hitherto been a very laborious, expensive and time-consuming procedure, which can only be carried out in suitably equipped laboratories and with skilled personnel.

A free radical is in an atom or group of atoms containing at least one unpaired electron. Electrons are negatively charged particles that usually occur in pairs, forming a chemically stable arrangement. If an electron is unpaired, another atom or molecule can easily bond with it, causing a chemical reaction. Because they join so readily with other compounds, free radicals can effect dramatic changes in the body, and they can cause a lot of damage. Each free radical may exist for a tiny fraction of a second, but the damage it leaves behind can be irreversible.

Free radicals form in many different ways. One of the most common is for oxygen to react with different chemical substances in the body, including fats. Called "oxidation", this process is what occurs when metals rust or when fats become rancid. Although oxygen is crucial to life, in certain oxidation reaction, such as those involving polyunsaturated fats, oxygen can release the energy of the fats and in doing so created free radicals, known in this case as "oxygen radicals". Oxygen radicals are highly volatile, dangerous molecules, rushing around madly to unload this excess energy, and in the process inflicting damage on protein, fats, and nucleic acids, including the DNA within cells.

Free radicals are normally present in the body in small numbers. Biochemical processes naturally lead to the formation of free radicals, and under normal circumstances the body can keep them in check. Indeed, not all free radicals are bad. Free radicals produced by the immune system destroy viruses and bacteria. Other free radicals are involved in producing vital hormones and activating enzymes that are needed for life. One needs free radicals to produce energy and various substances that the body requires. If there is excessive free radical formation, however, damage to cells and tissues can occur. The formation of a large number of free radicals stimulates the formation of more free radicals, leading to more damage.

The presence of a dangerous number of free radicals can alter the way in which the cells code genetic material. Changes in protein structure can occur as a result of errors in protein synthesis. The body's immune system may then see this altered protein as a foreign substance and try to destroy it. The formation of mutated proteins can eventually damage the immune system and lead to leukemia and other types of cancer, as well as a host of other diseases.

In addition to damaging genetic material, free radicals can destroy the protective cell membranes. The formation of free radicals can also lead to retention of fluid in the cells, which is involved in the aging process and many other diseases. Free radicals are a powerful enemy in our battle to maintain health. Free radicals attack the body's defenses, weakening them so that they will not properly protect us. Research has established that free radicals can damage healthy body cells.

The production of free radicals is 100% normal. It goes along with breathing. But there are things that cause a person to make more free radicals than they normally would. A non-limiting list includes:

- Stress emotional or physical stress makes one breathe less and burn energy more. Stress feeds on anaerobic metabolism, not oxygen.
- Ozone in the air—a great way to produce superoxide.
- Auto exhaust—one breathes carbon monoxide and hydrochloric acid instead of oxygen.
- Cigarette smokes—similar to auto exhaust.
- Inflammation—your body's immune system creates free radicals as it fights germs.
- Radiation—alters molecules in subtle ways, throwing off free radicals.
- Sunlight—a form of radiation.
- Impure water—between the impurities left in municipal water supplies and the chemicals used to cover them up, most water is toxic out of the tap. Beware that bottled water may come from the exact same source.
- Processed foods—you can't get nutrients from man-made food, so your body shifts to anaerobic metabolism to try to get something out of it.
- Toxic metals—they are in our soil, our water, our air, and they attract free radicals.
- Industrial chemicals—in general, man-made chemicals are bad for you.
- Drugs—even the "safe" ones the doctor prescribes for you changes a person's ability to metabolize oxygen.

Free radicals have a penchant for attacking certain parts of the cell. Damage to these specific areas creates its own set of problems.

The cell wall: it is normally porous, allowing nutrients into the cell and letting waste products out. When attacked, it can either rupture and leak or become clogged. Either way, the cell dies prematurely.

DNA: When free radicals are in the nucleus of the cell, they are apt to attack the generic material that the cell uses to reproduce itself. Sometimes a free radical will simply attack a gene and mess up this information, which is encoded by subtle chemical bonds. Another type of damage is called cross-linking, in which the DNA is linked to a protein chain so that it cannot replicate at all. These are now seen as the leading mechanisms for cancer growth.

Blood and tissue lipids: Through a process referred to as lipid peroxidation, fatty cells in the blood and hydrogen peroxide or peroxynitrate (both are ROS) attacks tissues. An example is low-density (LDL) cholesterol which, when damaged by free radicals altered by your immune system, becomes a bloated, sticky blob that forms an obstructing plaque in the arterial wall. This hardening of the arteries (arteriosclerosis) is a leading cause of heart disease and stroke. Fats that have been peroxidized can also become rancid and toxic to your body.

Motochondria: The powerhouses of the cell, where cellular energy is created. If their reactions are interrupted by free radicals, than the cell does not have energy to work. As cells with low energy accumulate, you eventually have whole body that is low on energy, tired all the time, and having trouble fighting off disease.

Lysosomes: Lysosomes are little packets of enzymes inside the cells. These enzymes are designed to eat though anything except the membranes that contains them. When their membrane is rupture by ROS damage, those enzymes proceed to eat through that cell, and the one next to it, and the one after that, and they produce more free radicals as they go.

As we have seen many different factors can lead to the production of free radicals. Exposure to radiation, whether from the sun or from medical x-rays, activates the formation of free radicals, as does exposure to environmental pollutants such as tobacco smoke and automotive exhaust. Diet also can contribute to the formation of free radicals. When the body obtains nutrients through the diet, it utilizes oxygen molecules containing unpaired electrons are released. These oxygen free radicals can cause damage to the body if produced in extremely large amounts. A diet that is high in fat can increase free radical activity because oxidation occurs more readily in fat molecules that it does in carbohydrate or protein molecules. Cooking fats at high temperatures, particularly frying foods in oil, can produce large numbers of free radicals.

Substances known as antioxidants neutralize free radicals by binding to their free electrons. By destroying free radicals, antioxidants help to detoxify and protect the body. There are other free radicals that can show up. To deal with all oxidative damage caused by free radicals, it is important that one have enough antioxidants in their system. A person has the capacity to handle a lot more ROS than they are creating; to help maintain not only health, but youth and vitality as well.

Free radicals are molecules that have been chemically damaged (modified) by removing a single electron. If this happens to special molecules in the body such as DNA, RNS, membrane lipids and lipoproteins or enzymes their actions in the body may be affected. The end result can be poor cell function (disease) control of cell death (apoptosis) or even tissue death (necrosis). Many, if not all diseases, afflict the body through oxidative damage. The free radical theory of aging says it is the primary cause of aging itself.

Free radicals are simply unpaired electrons. Electrons like to be electrically neutral. When they are not they quickly look for something to latch on to thereby creating a new molecule. This is how many chemical reactions take place. Without these oxidation-reduction reactions, not only would life not take place, but also many of the other important functions of the body would not either. For example, which blood cells often kill their bacteria or viral enemies with free radicals?

Free radicals are like fire. Properly confined they are beneficial to the body and, fortunately, the body has means to confine them. These are called antioxidants, and they look for excess free radical activity and neutralize it. It is only when free radicals become unconfined and excessive and start attacking normal, healthy tissue that disease takes place. This happens when antioxidant activity is inadequate, hence the importance of maintaining proper antioxidant activity in the body.

A large number of methods for the detection of Malondialdehyde and other related aldehyde in the blood have been described in the past. These may be divided into five main classes: (a) Direct or indirect specto-photometric methods; (b) Spectrofluororimetric methods; (c) Chemiluminescent methods; (d) Chromatographic methods; and (e) Electrochemical methods. All such methods pose problems of specificity of instrumental complexity, which preclude their routine used by non-specialized laboratories.

Free radicals can attack the cells of your body, affecting cardiovascular, neurological and immune systems. Higher level of free radicals has been associated with a number of age-related and chronic diseases such as diabetes, cardiovascular and pulmonary diseases and cancer.

Antioxidants help prevent damage to our organs by inhibiting the oxidation of cells and body fluid. Our body, cells continuously generate reactive oxygen species and other free radicals as a result of metabolic processes. Antioxidants are essential to our body's defense against free radicals that can attack the cells of the body, affecting the cardiovascular, neurological and immune systems. Antioxidants react with these free radicals and neutralize them.

Antioxidants are enzymes, vitamins and minerals that mop up free radicals, which are molecules in the body that contain one or more unpaired electrons in their orbits. These unstable molecules destroy healthy cells in an attempt to stabilize themselves. This process damages healthy cells, sometimes beyond repair. Left to run rampant, free radicals, can batter our proteins, cell membranes, and then reach the cell core of DNA. They can clog the walls of our arteries, kill brain cells, stiffen and deplete our muscles, and throw our immune systems out of kilter. The damage done to enzymes, cell membranes, and DNA may lead to the development of several serious conditions, including heart disease, Alzheimer's disease, cancer, arthritis and others.

To protect itself against free radicals damage, the human body requires antioxidants. We produce some antioxidants internally, others we ingest in the foods we eat. Antioxidants disarm free radicals in a variety of ways and then other body chemicals mop up the remnants of these once-harmful molecules before they can do any damage to the body. Among the most important antioxidants are the vitamins C, E, and beta-carotene (a precursor of vitamin A), glutathione, selenium, that work to protect our cells from free radical damage. Antioxidants scavenge and neutralize the free radicals in our body and convert them to non-toxic chemicals.

Malondialdehyde represents a measure of free radicals, specifically aldehyde free radicals from lipid peroxidation. The higher the malondialdehyde value in the urine, the greater the amounts of aldehyde free radicals, and thus the greater the degree of lipid perioxidation. Conversely, lower malondialdehyde levels reflect decreased lipid peroxidation and thus less oxidative stress to the body.

Highly active and dangerous chemical groups (free radicals) cause the damage to our cells and tissue that is at the root of most diseases. Free radicals are constantly being formed in the body as a result of basic disease processes. Unfortunately outside scientific and medical circles the subject of free radicals harm to our body is not widely understood.

The following are some conditions either caused or contributed to by free radicals: Aging, Angina, Brain Damage, Cancer, Cataract, Common Cold, Heart failure, Heart attack, Kidney disease, Male infertility, Malnutrition, Poisoning, Radiation sickness, Retinopathy, Rheumatoid arthritis, Stroke.

Oxidative stress is the negative effect created in the body by free radicals and has been intensified as a major factor in the progression of aging and diseases. The life of a free radical has three stages, the initiation stage, propagation stage and finally the termination stage. Free radicals are terminated or neutralized by nutrient antioxidants, enzymatic mechanisms, or by recombining with each other. The quest is to find that delicate balance between free radical activity and optimum antioxidant therapy, thus achieving homeostasis.

Antioxidants are known to counteract these damage-causing radicals. Examples of few antioxidants used by the body are vitamins $B_1$ (Thiamine), $B_2$ (Riboflavin), $B_3$ (Niacin), $B_5$ (Calcium Pantothenate), $B_6$ (Pyridoxine Hydrochloride), $B_{12}$ (Cyanocobalamin), C (Ascorbic Acid), $D_1$ (Alpha Tocopheril Acetate), $D_3$ (Ergocalciferol) and Vitamin E, 11 Acetyl-1-cysteine, Carotenoids, Lipoic Acid, Melatonin, Albumin, Omega-3, Lycopene, Flavonoids, Thiols, Resveratrol, Pyconogenol, Betacarotene (Provitamin A), L-Glutathione, CoQ10 (Ubiquinone), Papain, Papaya Fruit, Resveratrol, Lycopene, Selenium (Selenomethionine), Zinc Sulfate, and n-acetyl-1-cysteine.

Antioxidant compounds must be constantly replenished since they are "used up" (converted) in the process of neutralizing free radicals. Long-lived individuals and various animal species have been shown to have lower levels of free radicals. The body's defenders against free radicals are known as antioxidants. They scavenge and neutralize the free radicals converting them to non-toxic chemicals in the body.

Measuring the level of these free radicals form the oxidation of lipids indirectly indicates whether one's body has enough antioxidants to protect itself from free radicals. Therefore, one must continually produce more of the antioxidants in the body or ingest them either in our diet or by supplementation. Repair enzymes that can regenerate some antioxidants are Superoxide Dismutase, Bromelain, Papain, Protease, Amylase, (SOD), Glutathione, Peroxidase (GPX), Glutathione Reductase (GR), Catalase and other metalloenzymes.

Antioxidants must also be of different types so that they might be available for action when and where they are needed. When must ingest a variety of different types of antioxidants, along with other important nutrients to impact the damaging effects of the generation of free radicals by the body. This is best done through a proper balanced diet that is augmented by mineral/vitamin supplementation when needed.

In order to scavenge free radicals the human body has developed several "defense" systems. Our body uses antioxidants to "neutralize" the free radicals. These can be our own international enzymes such as catalase or superoxide-dismutase. As important are the antioxidant nutrients in our food or food supplements. Such external antioxidants are often, however, depending on life style and specific environmental conditions of the individual, not available in sufficient quantities so that free radicals may not be neutralized to the extend which the body requires.

Antioxidants help prevent damage to our organs by inhibiting the oxidation of cells and body fluid. Our body's cells continuously generate reactive oxygen species and other free radicals as a result of metabolic processes. Antioxidants are enzymes, vitamins and minerals that mop up free radicals, which are molecules in the body that contain one or more unpaired electrons in their orbit. These unstable electrons damage healthy cells, sometimes beyond repair. Left to run rampant, free radicals can batter our proteins, cell membranes, and then reach the cell core of DNA. They can clog the walls of our arteries, kill brain cells, stiffen and deplete our muscles, and throw our immune system out of kilter. The damage done to enzymes, cell membranes, and DNA may lead to the development of several serious conditions, including heart disease, Alzheimer's disease, cancer, arthritis and others.

To protect itself against free radicals damage, the human body requires antioxidants. We produce some antioxidants internally, others we ingest in the foods we eat. Antioxidants disarm free radicals in a variety of ways and then other body chemicals mop up the remnants of these once harmful molecules before they can do any damage to the body. Among the most important antioxidants are the vitamins C, E; and betacarotene (a precursor of vitamin A), glutathione, selenium that work to protect our cells form free radical damage, which is why it is so important to evaluate your intake and make adjustment if necessary. Doing so could help you maintain your health and feel more vital. Antioxidants scavenge and neutralize the free radicals on our body and convert them to non-toxic chemicals.

Free radical production is a natural occurrence in cells, especially in cells that use or are exposed to oxygen. Too much production or production in the wrong place can be harmful, both now (acutely) and in the future (chronically). The body needs antioxidant compounds to serve as a source of electrons to free radicals without damaging the cell components.

Self-monitoring free radicals in excessive quantities may play an important role in the overall health care, because indicate that one's body has not antioxidants to protect itself from free radicals. The present invention was designed to allow for such self-monitoring.

SUMMARY OF THE INVENTION

The present invention generally provides a free radical urine test kit which can be performed by a user in his or her home. The test kit of the present invention is effective to determine and monitor free radicals excess in the urine, called oxidative stress caused damage to cell proteins, lipid and DNA. Higher level of free radicals has been associated with a number of age-related and chronic diseases such as diabetes, cardiovascular, pulmonary diseases, cancer, etc.

These and other objects and advantages will be apparent from a consideration of the following disclosure. In accordance with the invention, it has now been found that diagnostic agents for the detection of the level of free radicals in the body by monitoring the presence of malonyl-aldehyde components in urine, which are outstanding useful and can be prepared in a substantially simpler and more economic manner than possible heretofore, are obtained by blending the urine with a chromogen as suitable reactant to rapidly permit a visual detection of the quantitative determination of the concentration of Malondialdehyde and other Aldehyde.

The invention relates to a diagnostic agent for the detection of Malondialdehyde and other Aldehyde in the morning urine, which are formed in the course of the lipid peroxidation pro process caused by the free radicals, and more particularly having to do with a process for the preparation of such test, including formulations of antioxidants as body's protectors against oxidative stress and help reduce the risks of developing free radicals diseases. The higher the malondialdehyde value in the urine, the greater the amounts of aldehyde free radicals, and thus the greater the degree of lipid peroxidation. Conversely, lower malondialdehyde levels reflect decreased lipid peroxidation and thus less oxidative stress to the body.

The invention relates to diagnostic agents for the detection of malonyl-dialdehyde and other aldehydes in urine and more particularly relates to a colorimetric test kit for use in monitoring urine levels of by-products of fatty substances damaged by oxidizing agents in the body and a method for using the same.

A primary purpose of the present invention is to determine free radicals in urine by simple means, i.e., by the naked eye. "Determination of oxidative stress" is defined in this connection as obtaining a quantitative statement on the concentration and presence of free radicals in the human body, i.e., on the oxidative loading of the organism. The malonic dialdehyde in the urine serves as the indicator substance, object of the present invention.

By means of the present free radical urine test kit, the urine after reacted with a chromogenic substrate will develop a colored derivative from light to straw, than from purple to red, to a very red, to a severe red, depending of the Malonyldialdehyde and other aldehydes concentration, which are directly correlates with detected color intensity.

The present invention provides a new and improved free radical colorimetric test kit for the use in detecting Malonyldehyde and other aldehydes in urine. The present invention provides a novel do-it-yourself free radical test kit to employ for monitoring Malonyldehyde and other Aldehydes in urine, representing often a very serious case of oxidation stress. The present invention detects free radical activity in the body with simple urine collection.

In accordance with the present invention, it has been found that diagnostic agents for the detection of Malonyldialdehyde and other Aldehydes in urine which are outstandingly useful and can be prepared in a substantially simpler and more economical manner than possible heretofore, such as being obtained by blending the urine with chromogenic agents. The free radical urine test kit of the present invention determines cells damage by such potentially dangerous agents due to their oxidative attack able to trigger numerous diseases.

The present invention primarily is a simple quick test for visual determination of radical activity oxidative stress on the human organism. The urine test kit can measure the breakdown product of the free radical activity on the long chain polyunsaturated fatty acids (PUFA) found in the phospholipids, particularly those found in the phospholipids that are prominent in cell membranes. This breakdown product develops at the double bond at the extreme end of the PUFA. This gives a three-carbon compound that has an aldehyde group at both ends, namely malondialdehyde (MDA). MDA and other aldehyde breakdown fragments from PUFA reflect the direct activity of the free radical attack on PUFA.

The present invention relates to formation in a kit and method for determining free radicals status in urine. This invention relates in particularly to such a kit and such a method, in which the determination of free radicals status can be carried out extremely easily on the basis of the color reaction with a reagent selected from the group of chromogens by visual color comparison, i.e. with the naked eye.

All people who are exposed to free radicals increase Malondialdehyde level in the urine. Thus Malondialdehyde has shown to be a clinical biochemical marker for the detection of free radicals in varying degrees in the urine, easily ascertainable by visual evaluation. The present invention provides a novel effective procedures and chromogen which can be routinely employed by everyone, but particularly by any medical practitioner during each patients visit without the need of elaborate and costly facilities.

This invention relates to a kit and method for measuring urine levels of by-products of fatty substances damaged by oxidizing agents in the body. These highly reactive, unstable chemicals are known as pro-oxidants or free radicals, which are formed as part of a cell's use of outside sources such as inadequate diet and alcohol and exposure to environmental pollutants and ultraviolet radiation. This technological breakthrough measures the distant end of the polyunsaturated fat chain where aldehyde from as a result of free radical attacks to the cells. The test can coordinate with laboratory measurements to create precise results from the urine specimen. Aldehyde activity is much more concentrated in urine. The urine test is 50 times more sensitive than MDA Serum free radical tests. Free radical damage can lead to cell degeneration, initiating a host of diseases such as fatigue, arthritis, elevated cholesterol and degenerative heart disease. This test indicates the actual degree of damage to the cell by free radical activity. In the process of free radical production in the body, one of the byproducts is MDA (Malondialdehyde) most accurate measurement of MDA is in the urine as confirmed through complex and sensitive laboratory assay of MDA in the urine compare to MDA in the blood has been ascertained that MDA in the blood is quickly cleared from the body by the kidneys, therefore the urine is preferred because it is where the body fluid to measure MDA is concentrated, the urine therefore is the ideal body fluid to measure MDA and thus a very sensitive way to look for free radical activity.

Malondialdehyde represents a measure of free radicals, specifically aldehyde free radicals from lipid peroxidation. The higher the malondialdehyde value in the urine, the greater the amounts of aldehyde free radicals, and thus the greater the degree of lipid peroxidation. Conversely, lower malondialdehyde levels reflect decreased lipid peroxidation and thus less oxidative stress to the body. The free radical test is an effective non-invasive urine test that measures the amount of free radicals oxidants in the body within a minute. This test enables the user to measure the amount of oxidative stress the body is enduring and the results of antioxidants intervention.

The present test measures the amount of a free radical called malondialdehyde (MDA) in the urine. It is a measure of the overall antioxidant capacity in the body. The test is believed to be 50 times more reliable than a MDA blood test. Accuracy is within the range of about 95%. The test is conducted by comparing the color change in a urine sample with a colormetric chart. The invention provides a rapid do-it-yourself and inexpensive urine test kit for detecting free radicals. The free radical test kit is a safe, easy to use and reliable screen that uses a urine collection to measure your free radical levels.

The test kit of the preset invention is effective to determine and monitor free radicals excess in the urine, called oxidative stress caused damage to cell proteins, lipid and DNA. The present diagnostic urine test is outstandingly useful and can be prepared in a substantially simpler and more economic manner than possible heretofore. When contacted with urine containing malondialdehyde and/or other aldehyde such do-it-yourself test kit gave a positive reaction in one minute as evidenced by the change in color. The higher the concentration of the malondialdehyde, the deeper the color produced, when no malondialdehyde is inside the urine, the same does not undergo a color change.

Self-monitoring Free Radicals in excessive quantities may play an important role in the overall health care, because indicate that one's body has not antioxidants to protect itself from free radicals. The present invention provides a way to help to evaluate your intake and make adjustments if necessary. Doing so could help you maintain your health and feel more vital.

The do-it-yourself urine free radical test kit, object of the present invention is very simple to use and effectively quantitatively assess the activity of free radicals in the body by detecting the difference in color. When the urine color is very dark suggest a high free radical activity, and the clear or light pink color indicates low free radical activity. By controlling these results, one may evaluate the necessity to protect the body against free radicals and reduce oxidative stress by taking synergistic antioxidants as food supplement.

The present do-it-yourself free radical urine test kit is not intended to diagnose, treat or cure any disease. Its value to everyone is that it is only to point out the way to adjust one's life style by supplementing with antioxidants to help make changes that enhance to antioxidants stores and attempts to decrease those factors that induce and generate the injurious free radicals by scavenging and neutralizing the same into non-toxic compound to provide an immediate health benefits.

The goal is then to have optimum antioxidant levels, which can be reflected, by minimal or low free radical activity, preventing damage to our organs and boosting the immune system.

The free radicals testing capabilities of the present invention provide a user with valuable data for correlating highly reactive activity with specific disease processes, and can help to determine appropriate, specific antioxidants and nutritional protocols needed to counteract free radical damage and those disease processes.

The composition of the novel test kit of the present invention enhances, preferably significantly, the sensibility of the colormetric scale in comparison to other commercial kits. The test kit may include one or two plastic or glass bottles, to formulate the chromogens and solvents all together in liquid form all in one bottle, or in separate way in two bottles. In the latter case, it may be necessary that one bottle contain only the formulation with the chromogen and solvents mixture in a powder form, and a second bottle to contain the DMSO in a liquid form, to be blended at the time of the test with the content of the first bottle and where than after insert in the morning urine in quantity as needed to reach the maximum mark line of the bottle to be analyzed for the presence of malondyldehyde or other aldehydes.

The choice of the final formulation in one or two bottles can depend on the request of the manufacturer and/or end user preference. The test kit to determine the radical free activity on the body, can include an evaluation color chart to be used for reading the resulting urine change in color to self determine the level of the oxidation stress which is causing damage to cell proteins, lipids and DNA.

The present urine test kit, without any effort, is simple and effective to determine and monitor free radicals by comparing the resulted color reaction on a predetermined chart, which by the intensity of the color show a high concentration of free radicals in the body. The present invention aid in self-monitoring the high presence of free radicals which are responsible for the onset and progression of many diseases, such as diabetes, cardiovascular, cancer, asthma, bronchitis, smoker's lung, liver and many others.

In the process of free radical production in the body there are certain chemical by-products produced. One of these products is malondialdehyde (MDA), which is the substance that produces the color reaction in the free radical test used as measuring mechanism. The free radical urine test of the present invention can be a self test that can be used to evaluate the oxidative stress affecting the body by determining levels of malondialdehyde, which is generated when free radicals attack unsaturated fatty acids and it is eliminated with the urine. The amount of malondialdehyde present can be determined by means of a color reaction. Morning urine is mixed with an indicator solution and the more intensive the red color, the greater the free radical stress that the body is exposed to. The free radical test under subject is a non-invasive urine test that measures the amount of free radicals in the body within few seconds.

"Free radical testing capabilities" provide: valuable data for correlating highly reactive free radical activity with specific disease processes to allow the user to determine appropriate specific antioxidants and nutritional protocols needed to counteract free radical damage and those disease process. The present invention relates to a kit and method for determining free radical activity in the body with simple urine collection. The urine relates in particular to such a kit and such a method in which the determination of free radical status can be carried out extremely easily on the basis of the color metric reaction with a reagent selected from the group of indwell derivatives by visual color comparison, i.e. with the naked eye.

The present invention provides a colorimetric test indicating free radicals on urine and test kit therefore. The present invention free radical urine test provides a colorimetric test to detect free radicals performed on urine samples. The composition for use in the test can be a mixture of chromogen as reagent, acid and solvents. The colored results of the exothermic reaction of the composition with the urine are evaluated through a color-comparison analysis on a predetermined chart.

The technological breakthrough for the free radical test (also known as the oxidative stress test) is the effectiveness and stability of the various ingredients used for the calorimetric (color absorbent) reading from urine testing, which has evolved from comparing color of the free radical urine test to color on a predetermined chart. In studies at a major university, it was determined that this new urine test is 50 times more sensitive than blood/plasma aldehyde testing.

The present invention includes the method, the compositions used in convenient kit containing the ingredients for performing the test by comparing the color change in a urine sample with a chart.

DETAILED DESCRIPTION OF THE INVENTION

Free radical self-testing of the present invention may also be a boon to consumers. The Free Radicals Urine Test will lower healthcare costs, help keep a closer watch on health conditions and make earlier detection of health problems possible. Several factors promote the present self-test-kit. These include, but are not limited to: (a) Relatively inexpensive tests, (b) Simple to-perform tests that can be done in complete privacy; and (c) Fairly reliable tests. When used as directed the present invention free radical test for purchase by the public can be safe and effective.

The present urine self-test may offer many health benefits to people of all ages. These include excessive quantity of free radicals that can be detected. This may spur smokers to stop smoking immediately, stop taking any drugs or medication that may be harmful or dangerous to their health, and inform user's whether it is necessary to seek early medical care to help provide a safer, happier life.

Measuring the level of free radicals can be easily observed with the present invention urine test and provides an efficient way to monitor the effectiveness of antioxidants treatment. At home the free radicals test offers an easy effective way of monitoring urine to possibly help millions of people to control their health condition.

While the present invention has been described with reference, the various ingredients may include at least two chromogens, chelating agents, solvent, and stabilizing substance to be blended inside the urine container, it will be understood by those skilled in the art, without departing from the spirit of the invention, such composition may comprise, but not limited to one or more of the following: the water miscible organic solvents hereof should be selected from: schiff agent, acetamide, dimethysulfide, isopropanol, dimethylformamide, dioxane, ethanol, formamide, hexamethyl, phosphoric triamide, hydrochloric acid, methylene blue, n-methylacetamide, methanol, soluted tioxane or tetrahydrofurane, p-toluenesulfinic acid (TsOH).

Further according to the present invention the chromagen hereof can be selected from or comprise two or more of the following: Pararosaniline sulfhate, pararosaniline hydrochloride, basic fucsin, basic parafucsin, basic red 9, magenta 0, parafuchsin hydrochloride, paramagenta hydrochloride, (DETBA)=1,3 diethyl-thiobarbituric acid, 2-thiobarbituric acid, 1,2 dimethylindole, 2-dimethylndole, n2ndimethyl-para-phenylenediamine sulfonate, and n, n dimethyl-para-penilediamine oxalate, but after numerous tests the preferred and most effective chromogens are the following: 1,2 dimethylindole and para-rosaniline hydrochloride, but only when are used jointly in the same composition.

The possibility of using a mixture of the above reagents has been investigated in order to observe possible synergic effects. After numerous experiments the best results were obtained with the combination of the three following reagents:

Pararosaniline as reagent is widely reported in the literature, pararosaniline sulfhate (basic Fuchsin) allows the colorimetric determination of MDA in urine.

The Schiff reagent is obtained from Fuchsin in the presence of a source of $H_2SO_3$ ($SO_2$ in water, sodium metabilsulfite.). Contrary to Fuchsin, the Schiff reagent is colorless, whereas their reaction products with aldehydes are reddish (variable).

1,2 Dimethylindole is used carrying methyl or phenyl substitute together with different acids as reagent for MDA. From the U.S. Pat. No. 6,835,554, it seems that methyl derivatives do not give appreciable color changes with MDA at concentration in the range 1-10 uM. The possibility of a bi-dimensional test by adding different amounts of MDA to urine samples with different colors is also cited. The color obtained from the reaction depends on indole substitutes. For example, the N-methyl 2-phenyl indole has a maximum absorption at A=532 nm; the reaction needs heating at 100 C for 20 minutes. The colorimetric reaction may take place within 15-30 min at room temperature: the MDA concentration is determined by comparing the solution to a colorimetric scale.

The 1,3-diethyl-thiobarbituric acid (DETBA) as reagent. DETBA gives colored adducts with MDA in the presence of several different solvents.

The Thio-Barbituric acid (TBA) reacts with MDA in a 2/1 ration leading to red fluorescent derivatives. The maximum absorbance of the adduct is at 586 nm. The use of the Bioxytech LPO-586 kit has been reported where the urine is mixed with a solution of TBA and then warmed at 45° C. The use of TBA with glycolic acid, to reveal MDA, has been used on paper strips and warmed up to 100° C. TBA does not give a selective reaction because it gives colored adducts also with non-aldehyde derivatives, generally identified as TBARS (Thio Barbituric Acid reactive Substances), DTBA has been applied to the determination of MDA in urine and plasma by fluorescence or chemiluminescence methods. It gives adducts similar to those obtained from TBA but with a lower polarily, so that these adducts can be easily separated by HPLC from other components.

By means of UV/VIS or fluorescence measurements it is possible to get sensibilities in the order of pico or phentomoles/liter. The problem of the poor selectivity is unresolved. On the ground of the above reported information and considerations, the experimental work has been devoted to check the reactivity of each of the above reagents toward MDA dissolved in urine. The aim was to set up the better reaction conditions for the above reagents as far as it concerns the reaction time, detection limit and stability of them. The results obtained are reported in the following section.

In conclusion these experiments confirmed that the use of a mixture of the above reagents will give a positive advantages at the concentration at which each of them may give a positive result. The composition of the present invention where the addition to DETBA of the Pararosaniline and the 1,2-Dimethyllindole will improve considerably the reaction. In all these experiments the color intensity has higher up than using the single reagents. The experimental results obtained in the first screening approach allowed focusing interest, on DETBA, Pararosaniline sulphate, and 1,2 Dimethyllindole as reagent. The use of Methylene Blue can be interesting feature of the kit because it helps enhance significantly the sensibility of the colorimetric scale, also in comparison to the other commercial kits.

To overcome the above mentioned difficulties and obtaining by the way, a formulation having an additional novelty, it is possible to formulate the reagents in a separate way: (1) In a powder form or as a solid tablet containing the solid reagents DETBA with or without other reagents with TsOH; and (2) A liquid solution of DMSO containing one or more of the above reagents. The system will operate by dissolving the solid in the liquid (the dissolution is almost immediate) and then adding the urine sample. An alternative solution of the problem can be the use of a DMSO gel to entrap the whole reagents. It is likely that this may improve the stability problems. On the ground of the obtained experimental results it is possible to suggest the following formulation to prevent or cure the oxidative stress that may result from the analysis of the urine.

A proposed formulation by way of illustration only, can comprise, but is not limited to: about 30 mg of DETBA; about 0.01 mg of Pararosaniline sulphate; about 0.01 mg of 1,2 Dimethylindole; about 160 mg of TsOH; about 0.01 mg of Methylene blue; and about 2 ml of DMSO.

Rather than guessing if an antioxidant program is working or whether it is working too well, the present invention test can provide a scientific measurement of results. To assess the toxic damage to the body by such determination of the load of malondialdehyde exerted by free radicals, such operation should be carried out by the patient himself/herself without major expenditure, quickly and at low cost. Such a determination may therefore be carried out on the basis or urine samples in particular.

The present invention do-it-yourself urine free radical test kit is very simple to use and effectively quantitatively assess that activity of free radicals in the body and by detecting the difference in color. The colorimetric test kit can monitor free radicals oxidation of the low-density lipoproteins (LDLS) by blending the urine sample with at least one of the disclosed chromogens. The malonyldialdehyde and other aldehydes in the urine may combine with the chromogens and this reaction alters the color of the chromogens of this test, the colorless solution turns to various shades from light, to a dark red hue (as per table 1)

TABLE 1

Test to be done on first morning urine
Color chart for evaluation of the free radical test (FRA)

| | | |
|---|---|---|
| 1. | Very low FRA (optimum) Maintain current diet and antioxidant levels Repeat the test in one month | Bright |
| 2. | Low FRA Continue current diet and slightly increase intake of Antioxidants Repeat test in two weeks | Straw Colored |
| 3. | Medium FRA Excess Free radicals. Improve diet and increased intake of Antioxidants. Repeat test in two weeks. | Pinkish |
| 4. | High FRA Improve diet and take high dosage of Antioxidants. Repeat test in one week | Pale Red |
| 5. | Excessive FRA Correct meliorating your diet and take higher dosage of Antioxidants Repeat test in one week. | Red |

The day before prior to using the test no drug or supplemental vitamins should be taken, because they may interfere with urine color. If the quantity of free radicals produced is superior to the physiological process, our body antioxidant system is no longer able to neutralize this excess, and so free radicals attack the cells, provoking oxidative stress damage which can be more or less serious.

When urine color is very dark suggest a high free radical activity, and the clear or light pink color indicates low free radical activity. By controlling these results, one may evaluate the necessity to protect the body against free radicals and reduce oxidative stress by taking synergistic antioxidants as food supplement.

The present invention do-it-yourself free radical urine test kit allows one to point out the way to adjust his or her lifestyle supplementing the diet with antioxidants to help make changes that endurance to antioxidants stores and attempts to decrease those factors that induce and generate the injurious free radicals by scavenging and neutralizing the some into non-toxic compound to provide an immediate health benefits.

The goal is then to have optimum antioxidant levels, which can be reflected by minimal or low radical activity, preventing damage to our organs and boosting the immune system.

The composition can comprise at least active substances, being homogeneously incorporated into any such substances in liquid or solid state. The color scale is included, so that the color comparison between the sample solution and the color scale can be done immediately and visually comparing the coloration of the urine sample with the color-scale, thereby determining the specific liquid peroxidation decomposition to evaluate the status of the body, so that countermeasures can be taken, strengthening the anti-oxidative defense by taking appropriate antioxidants supplements.

The following examples are provided in order to further demonstrate the concepts and advantages of the present invention. The examples are intended only to be illustrative of how to make and use the invention, and are not to be interpreted as limiting its scope in any way. All percentage expresses herein are by weight, unless otherwise indicated.

Antioxidant supplements as a source of life, include a wide variety of products. The Free Radical Urine Test is an aid to make this determination. The test provided a road map for the proper amount of Antioxidants as super defense therapy in eliminating Free Radicals in the body and enhancing the immune system based on scientific evidence rather than guesswork.

The formulas of the present invention have been carefully researched, reviewed and updated. Such research has taken over thirty years of study, work to put together, to provide people and health care professional with a more natural approach to healing, which may be used to reinforce the immune system and to scavenge free radicals. Antioxidants work synergistically, no single antioxidant protects all body systems, rather each one has protective properties for particular body parts or function. Products that combine two or more of such vital nutrients, as mentioned in the present invention are ideal to formulate a balanced multiple composition very effective as free radical scavenger and to protect all body systems.

When results show unwanted oxidative stress, the antioxidants may help to protect the body against the toxic damage caused by to the cells by free radicals. While the present invention has been described with reference to an Antioxidants formulations, it will be understood by those skilled in this art, without departing from the spirit of the invention, such antioxidants may comprise, but not limited to one or more of the following Acetyl-L-Carnitine; Acetyl-1-cysteine; Adenosine; Allicin; Aloe; Alpha Lipoic Acid; Anthocyanidins; Ascorbic Acid; Betacarotene; BTA; BHT; Bilirubin; Bilberry; Bioflavonoids; Burdock; Capsaicin; Catalases; Catechin; Cysteine; Coenzyme Q10; Copper Sebacate; Coumarin; Cryptoxanthin; Curcumin; Dimethylglycine; Ferrous Fumarate; Folic Acid; Garlic; Genistein; Ginger; *Ginkgo Biloba*; Gallates; Glycine; Gluconate; Glutathione or Glutathione Peroxidase; Green Tea; Inositol; Isoascorbic Acid; L-Glutamine; Linoleic Acid; L-Methyl Methionine; L-Seleno Cysteine; L-Seleno Methionine or Mthionate; Lycopene; Lutein; Manganese; Melatonin; Methionine Reductase w/(Cu—Zn or Mn); Milk Thistle; N-Acetylcysteine or L-Cysteine; N-Acyl 1-Cysteine Esters; N-Acyl 1-Methionine Esters; Papain; Papaia; Polyphenols; Poplar Bud, Procyanidin; Pycnogenol; Resveratrol; Rosemary; Rutin; Rutinose; Selenium-Yeast; Seleno cysteine; Seleno Methionine or Methionate; Sflybun Marianum; Sodium Bisulfite; Sodium Metasulfite; Sodium Sulfite; Sodium Thiosulfite; Spirulina; Sulfuraphane; Superoxide Dismutase (SOD); Taurine; Thioglycerol; Thiol; Thiosorbitol; Thiourea; Turmeric; Vitamin A Compounds; Vitamin $B_2$; Vitamin $B_{12}$; Vitamin C; Vitamin E; Wheat Grass; Zinc Gluconate; and Zeaxantin.

Another type of controlled release formulation, which may be used, is that which is produced by a process involving micro-encapsulation techniques. The following are examples of compositions prepared in accordance with this invention, but it is to be understood that they are presented by way of illustration only, and the dosage form for disease prevention may vary according to the nature of the condition being treated, and should not be in anyway construed to limit the scope of the present invention.

A nutraceutical formulation prepared according to the present invention consisting in Antioxidants in a dry powder form of liquid form, which comprises the percentages hereinafter described or fraction thereof: From approximately 0.0001 grams to a maximum of approximately 3 grams per day.

Some of the benefits and/or advantages of the present invention composition and method include, but are not limited to, the following:
1. Novel Antioxidants formulations derived from one or more vitamins, minerals, amino acids, enzymes, chemicals, hormones, plants extracts, proteins, etc.
2. Antioxidants formations of benefit 1, endowed with the "Radical Scavenger effect" for keeping our body healthy.
3. Therapeutic nutraceutical antioxidant formulations of benefit 1, effective to prevent and/or slow the progression of diseases.
4. An Antioxidants formulations of benefit 1, useful to prevent or to relieve many diseases such as: Alzheimer's disease, Arthritis, cancer, cataracts, Diabetes, Heart and blood vessel diseases, Hepatitis (all forms), immune weakness, inflammatory disorders, Macular degeneration, Parkinson's Disease, and to delay the onset of premature aging.
5. A nutraceutical Antioxidants compound of benefit 1, which may deliver health benefits beyond basic nutrition.
6. Novel Antioxidant compositions of benefit 1 effective in preventing or curtailing very early stages diseases.
7. The method of benefit 1 wherein said individual antioxidants dose should be in amount between approximately 0.0001 to 3 grams pro capita.
8. A composition for including one or more antioxidants as per benefit 1, may comprise one or more antioxidant with or without additives.

Having now generally described the invention, the same will be more readily understood through reference to the following examples which provided by way of illustration, and are not intended to be limiting of the present invention, unless specified. A wide range of equivalent parameters, concentrations and conditions can be used without departing from the spirit and scope of the invention and without undue experimentation.

The present invention provides a novel nutritional support for enhancing health life by restoring the nutrients that may be lost, scavenging free radicals, and to deliver extra strength for maintaining good health. The antioxidants compositions of the present invention can be presented in a new form suitable for oral ingestion. As one non-limiting example, the antioxidants to be blended may take the form of micro-powder granules, sparkling powder, gel, syrups, emulsions or suspensions. The composition of the present invention can be prepared to provide an effective dose of antioxidants having at least two or more active ingredients, each one being individually a powerful free radical scavenger with an amount at least sufficient for daily dosage requirement. Again, this can vary greatly depending upon the relative amount of the ingredients. The composition of the present invention can comprise at least two therapeutically active substances, being homogeneously incorporated into any such substance in a powdered state.

The following examples of compositions prepared in accordance with this invention, are by way of illustration only and the dosage form for disease prevention may vary according to the nature of the health condition being treated. These examples are not considered limiting in any manner the object of the present invention. Furthermore, the quantities suggested in the following non-limiting formulation examples may change (+ or −) by the Food Industries depending of the country where the invention is exploited because many foreign Ministries of Health have different regulation of the sale of food supplements. Therefore, the suggested quantities of antioxidants in the various formulations can be changed to apply to the maximum quantity required by the local foreign regulation.

| Formula n. 1 To resist Stress | |
|---|---|
| Vitamin A | 5000 I.U. |
| Carotene | 5000 I.U. |
| Thiamine | 50 mg. |
| Riboflavin | 50 mg. |
| Niacin | 50 mg. |
| $B_{12}$ | 100 mcg. |
| Biotin | 400 mcg. |
| Inositol | 100 mg. |
| PABA | 100 mg. |
| Vitamin C | 300 mg. |
| Bioflavonoids | 200 mg. |
| Vitamin E | 400 I.U. |
| Calcium | 300 mg. |
| Chromium | 200 mcg. |
| Magnesium | 50 mg. |
| Potassium | 200 mg. |
| Selenium | 100 mcg. |
| Zinc | 5 mg. |
| Methionine | 50 mg. |
| Glutathione | 100 mg. |
| Monosodium Glutamate | 50 mg. |
| Formula n.2 For Women | |
| Vitamin A | 5000 I.U. |
| Carotene | 5000 I.U. |
| Thiamine | 50 mg. |
| Riboflavin | 100 mg. |
| Niacin | 100 mg. |
| Folate | 800 mcg. |
| $B_{12}$ | 200 mcg. |

-continued

| | |
|---|---|
| Biotin | 400 mcg. |
| Choline | 100 mg. |
| Inositol | 100 mg. |
| Vitamin C | 500 mg. |
| Bioflavonoids | 200 mg. |
| Vitamin E | 800 I.U. |
| Calcium | 500 mg. |
| Manganese | 10 mg. |
| Iron | 20 mg. |
| Magnesium | 100 mg. |
| Potassium | 100 mg. |
| Selenium | 100 mcg. |
| Zinc | 20 mg. |
| Glutathione | 200 mg. |
| Formula n. 3 As Basic Supplement | |
| Vitamin A | 10,000 I.U. |
| Carotene | 20,000 I.U. |
| Thiamine | 50 mg. |
| Riboflavin | 50 mg. |
| Niacin | 50 mg. |
| $B_{12}$ | 100 mcg. |
| Biotin | 400 mcg. |
| PABA | 100 mg. |
| Vitamin C | 100 mg. |
| Bioflavonoids | 200 mg. |
| Vitamin D | 200 I.U. |
| Vitamin E | 200 I.U. |
| Calcium | 500 mg. |
| Chromium | 100 mcg. |
| Iodine | 100 mcg. |
| Magnesium | 50 mg. |
| Manganese | 10 mg. |
| Molybdenum | 50 mcg. |
| Potassium | 100 mg. |
| Selenium | 100 mcg. |
| Zinc | 30 mg. |
| Licopene | 10 mg. |
| Formula n. 4 for Maximum Performance | |
| Vitamin A | 5000 I.U. |
| Carotene | 5000 I.U. |
| Thiamine | 50 mg. |
| Riboflavin | 50 mg. |
| Niacin | 50 mg. |
| $B_{12}$ | 100 mcg. |
| Biotin | 400 mcg. |
| Vitamin C | 500 mg. |
| Bioflavonoids | 500 mg. |
| Vitamin E | 400 I.U. |
| Calcium | 300 mg. |
| Chromium | 200 mcg. |
| Iodine | 100 mcg. |
| Magnesium | 50 mg. |
| Manganese | 10 mg. |
| Potassium | 50 mg. |
| Selenium | 200 mcg. |
| Zinc | 30 mg. |
| Glutathione | 100 mg. |
| Valine | 50 mg. |
| Leucine | 50 mg. |
| Glycine | 50 mg. |
| Tyrosine | 50 mg. |
| Glutamic acid | 50 mg. |
| Tryptophan | 50 mg. |
| Lysine | 50 mg. |
| Aspartic acid | 50 mg. |
| Phenylanine | 50 mg. |
| Arginine | 50 mg. |
| Ornithine | 50 mg. |
| Formula n. 5 for Youth Extension | |
| Vitamin A | 5000 I.U. |
| Carotene | 5000 I.U. |
| Thiamine | 50 mg. |
| Riboflavin | 50 mg. |
| Niacin | 50 mg. |
| Folate | 400 mcg. |
| $B_{12}$ | 100 mcg. |
| Biotin | 400 mcg. |

-continued

| | |
|---|---|
| Glutathione | 200 mg. |
| Inositol | 100 mg. |
| Vitamin C | 500 mg. |
| Bioflavonoids | 500 mg. |
| Vitamin E | 200 I.U. |
| Calcium | 500 mg. |
| Chromium | 100 mcg. |
| Magnesium | 150 mg. |
| Manganese | 10 mg. |
| Selenium | 100 mcg. |
| Zinc | 10 mg. |
| Formula n. 6 Super Supplements | |
| Vitamin C | 1,000 mg. |
| Bioflavonoids | 200 mg. |
| Vitamin D | 200 I.U. |
| Vitamin E | 200 I.U. |
| Glutathione | 200 mg. |
| Calcium | 500 mg. |
| Chromium | 100 mcg. |
| Iodine | 100 mcg. |
| Magnesium | 250 mg. |
| Manganese | 10 mg. |
| Molybdenum | 50 mcg. |
| Potassium | 100 mg. |
| Selenium | 100 mcg. |
| Silicon | 100 mg. (horsetail grass) |
| Zinc | 30 mg. |
| Resveratrol | 3 mg. |
| Formula n.7 for Depression | |
| Inositol | 75 mg. |
| Vitamin A (betacarotene) | 800 mcg. |
| Vitamin D | 5 mcg. |
| Vitamin E | 10 mg. |
| Vitamin C | 10 mg. |
| Glutathione | 200 mcg. |
| Folic Acid | 200 mcg. |
| Vitamin $B_1$ | 1.4 mg. |
| Vitamin $B_2$ | 1.6 mg. |
| Niacin | 18 mg. |
| Vitamin $B_6$ | 2 mg. |
| Vitamin $B_{12}$ | 2 mcg. |
| Biotin | 100 mcg. |
| Pantothenic acid | 6 mg. |
| Choline | 50 mg. |
| SAMe | 200 mg. |
| Formula n.8 Essential Supplements | |
| Vitamin A | 3500 I.U. |
| (29% as Beta Carotene) | |
| Vitamin C | 60 mg. |
| Vitamin D | 400 I.U. |
| Vitamin E | 30 I.U. |
| Vitamin K | 25 mcg. |
| Vitamin $B_1$ (Thiamin) | 1.5 mg. |
| Vitamin $B_2$ (Riboflavin) | 1.7 mg. |
| Niacin | 20 mg. |
| Vitamin $B_6$ | 2 mg. |
| Folic acid | 400 mcg. |
| Vitamin $B_{12}$ | 6 mcg. |
| Biotin | 30 mcg. |
| Pantothenic Acid | 10 mg. |
| Calcium | 150 mg. |
| Iron | 10 mg. |
| Phosphorus | 75 mg. |
| Iodine | 150 mcg. |
| Magnesium | 100 mg. |
| Zinc | 15 mg. |
| Selenium | 20 mcg. |
| Copper | 2 mg. |
| Manganese | 2 mg. |
| Chromium | 120 mcg. |
| Potassium | 80 mg. |
| Boron | 150 mcg. |
| Nickel | 5 mcg. |
| Lutein | 250 mcg. |
| Lycopene | 30 mg. |
| Glutathione | 100 mg. |

-continued

| | |
|---|---|
| Omega3 | 30 mg. |

Formula n. 9 to Slow Aging

| | |
|---|---|
| Pycnogenol | 50 mg. |
| Coenzyme Q$_{10}$ | 15 mg. |
| Vitamin A | 5,000 I.U. |
| Vitamin C | 250 mg. |
| Vitamin E | 200 I.U. |
| Selenium | 50 mcg. |
| Cysteine | 500 mg. |
| Beta-carotene | 5,000 I.U. |
| Pantothenic acid | 250 mg. |
| Vitamin B$_6$ | 25 mg. |
| SOD (superoxide dismutase) | 50 mcg. |
| Methionine | 100 mg. |
| Glutathione | 100 mg. |
| Zinc | 15 mg. |
| Coenzyme | 30 mg. |
| Lycopene | 30 mg. |
| Pycnogenol | 30 mg. |
| Resveratrol | 3 mg. |
| Melatonin | 5 mg. |

Formula n. 10 for Healthy Vision

| | |
|---|---|
| Vitamin A (beta carotene) | 20.000 I.U. |
| Vitamin C | 500 mg. |
| Vitamin E (d-alpha tocopheryl succinate | 200 I.U. |
| Vitamin B$_2$ (riboflavin) | 25 mg. |
| Zinc (monomethionine) | 20 mg. |
| Selenium (amino acid complex) | 50 mcg. |
| Chromium (polynicotinate) | 120 mcg. |
| Citrus Bioflavonoid complex | 125 mg. |
| MSM (methylsulfonyl-methane) | 100 mg. |
| Lutein | 20 mg. |
| Zeazanthin | 5 mg. |

Formula n. 11 as Life Energy Enhancer

| | |
|---|---|
| Vitamin A (beta carotene) | 10.000 I.U. |
| Vitamin C | 1000 mg. |
| Vitamin D | 400 I.U. |
| Vitamin E | 200 I.U. |
| Vitamin K (Phylloquinone) | 80 mcg. |
| Vitamin B$_1$ | 25 mg. |
| Vitamin B$_2$ | 25 mg. |
| Niacin | 40 mg. |
| Vitamin B$_6$ (pyrodine HCl) | 25 mg. |
| Folate (folic acid) | 400 mcg. |
| Vitamin B$_{12}$ | 200 mcg. |
| Biotin | 100 mcg. |
| Calcium | 200 mg. |
| Iron | 18 mg. |
| Iodine | 150 mcg. |
| Magnesium | 100 mg. |
| Zinc | 15 mg. |
| Selenium (selenomethionine) | 25 mcg. |
| Copper | 0.5 mg. |
| Manganese | 4 mg. |
| Chromium | 20 mcg. |
| Monosodium glutamate | 50 mg. |
| Potassium | 50 mg. |
| Bioflavonoid | 60 mgt. |
| PABA (para-amino benzoic acid) | 15 mgt. |
| Carotenoids | 4 mgt. |
| Lutein | 3 mgt. |

Formula n. 12 for Arthritis and Muscle Pain

| | |
|---|---|
| Vitamin A (beta carotene) | 10.000 I.U. |
| Vitamin D (erocalciferol) | 400 I.U. |
| Vitamin B$_2$ (riboflavin) | 50 mg. |
| Vitamin B$_6$ | 10 mg. |
| Folate (folic acid) | 200 mcg. |
| Vitamin C | 500 mg. |
| Vitamin B$_{12}$ | 100 mcg. |
| Calcium | 500 mg. |

-continued

| | |
|---|---|
| Iron | 5 mg. |
| Phosphorus | 200 mg. |
| Magnesium | 25 mg. |
| Chromium | 30 mcg. |
| L-Cysteine | 100 mcg. |
| L-Methionine | 100 mg. |
| Sulphur | 25 mg. |
| Selenium | 50 mcg. |
| Zinc | 10 mg. |
| Methylsulfonylmethane (MSM) | 500 mg. |

Formula n. 13 for Golden Years

| | |
|---|---|
| Vitamin A | 10.000 I.U. |
| Beta-carotene | 15.000 I.U. |
| Vitamin B$_1$ | 50 mg. |
| Vitamin B$_2$ | 50 mg. |
| Vitamin B$_3$ (niacinamide) | 100 mg. |
| Vitamin B$_5$ | 100 mg. |
| Vitamin B$_6$ | 50 mg. |
| Vitamin B$_{12}$ | 300 mcg. |
| Biotin | 300 mcg. |
| Choline | 100 mg. |
| Folic acid | 800 mcg. |
| Inositol | 100 mg. |
| PABA (para-aminobenzoic acid) | 50 mg. |
| Vitamin C | 100 mg. |
| Bioflavonoids | 500 mg. |
| Rutin | 25 mg. |
| Vitamin D | 400 I.U. |
| Vitamin E | 600 I.U. |
| Vitamin K | 100 mcg. |
| Calcium | 500 mg. |
| Chromium | 150 mcg. |
| Copper | 3 mg. |
| Melatonin | 5 mg. |
| Iodine | 225 mcg. |
| Magnesium | 100 mg. |
| Manganese | 10 mg. |
| Molybdenum | 30 mcg. |
| Potassium | 99 mg. |
| Selenium | 200 mcg. |
| Zinc | 50 mg. |
| Coenzyme Q10 | 30 mg. |
| Garlic | 10 mg. |
| Omega-3 | 30 mg. |
| L-Cysteine (N-Acetyl-L-Cysteine) | 50 mg. |
| L-Glutathione | 50 mg. |
| SOD (superoxide dismutase) | 100 mcg. |
| Licopene | 30 mg. |

Formula n. 14 for Coronary Heart Disease

| | |
|---|---|
| Vitamin E | 400 I.U. |
| Folic Acid | 400 mcg. |
| Vitamin C | 1000 mg. |
| Coenzyme Q10 | 100 mg. |
| Omega-3 | 100 mg. |
| Resveratrol | 5 mg. |

Formula n. 15 for Hypertension

| | |
|---|---|
| Calcium | 1000 mg. |
| Magnesium | 400 mg. |
| Omega-3 fatty acids | 3 gr. |
| Garlic | 7 gr. |
| Coenzyme Q$_{10}$ | 100 gr. |

Formula n. 16 for Breast Cancer

| | |
|---|---|
| Coenzyme Q$_{10}$ | 100 mg. |
| Vitamin E | 800 I.U. |
| Flavonoids | 800 mg. |
| Melatonin | 0 mg. |
| Calcium | 1 gr. |
| Potassium | 100 mg. |

Formula n. 17 for Prostate Cancer

| | |
|---|---|
| Vitamin E | 400 I.U. |
| Lycopene | 50 mg. |
| Quercitin | 500 mg. |
| Selenium | 400 mcg. |
| Coenzyme Q$_{10}$ | 100 mg. |
| SOD | 30 Mg. |

-continued

| Formula n. 18 for Adult onset diabetes | |
|---|---|
| Alpha lipoic acid | 500 mg. |
| Chromium | 200 mcg. |
| Vanadyl sulfate | 5 mg. |
| Omega 3 fatty acids | 100 mg. |
| Gamma linoleic acid | 200 mg. |
| Chromium | 500 mg. |
| Garlic | 100 mg. |

| Formula n. 19 for Osteoporosis | |
|---|---|
| Calcium Citrate or Coral Calcium | 1000 mg. |
| Vitamin D | 800 I.U. |
| Magnesium | 200 mg. |
| Boron | 5 mg. |
| Vitamin K | 200 mcg. |
| Vitamin $B_{12}$ | −500 mcg. |
| Copper | 3 mg. |
| Zinc | 50 mg. |
| Bioflavonoids | 500 mg. |
| Betacarotene | 100 mg. |
| Zinc | 50 mg. |
| Vitamin C | 500 mg. |

| Formula n. 20 for Cholesterol | |
|---|---|
| Niacin | 800 mg. |
| Omega-3 | 50 mg. |
| Milk Thistle | 200 mg. |
| Vitamin E | 800 I.U. |
| Green Tea Powder | 100 mg. |
| Activated Charcoal | 100 mg. |
| Bran | 100 mg. |

| Formula n. 21 for Macular Degeneration Nutritional Formula | |
|---|---|
| Vitamin A (palmitate) | 1000 I.U. |
| Beta Carotene | 2000 I.U. |
| Vitamin $B_1$ (Thiamine) | 5 mg. |
| Vitamin $B_2$ (Riboflavin) | 5 mg. |
| Vitamin $B_3$ (Niacinamide) | 10 mg. |
| Vitamin $B_3$ (Niacin) | 2 mg. |
| Vitamin $B_5$ (Pantothenic Acid) | 20 mg. |
| Vitamin $B_6$ (Pyridoxine HCl) | 15 mg. |
| Folic Acid | 4 mcg. |
| Vitamin $B_{12}$ | 20 mcg. |
| Vitamin E (d-alpha Tocopherol) | 40 IU |
| N-Acetyl L-Cysteine | 40 mg. |
| Bilberry Extract | 10 mg. |
| Gikgo Biloba Extract | 10 mg. |
| Quercitin Bioflavonoid | 10 mg. |
| L-Taurine | 100 mg. |
| Calcium (Citrate) | 20 mg. |
| Magnesium (Citrate) | 40 mg. |
| Copper (Sebecate) | 600 mcg. |
| Selenium (Selenomethionine) | 40 mg. |
| Zinc (Picolinate) | 5 mg. |
| L-Glutathione | 5 mg. |
| Manganese | 1 mg. |
| Rutin | 3 mg. |
| Hesperidin | 2 mg. |
| Lycopene | 1 mg. |
| Lutein | mg. |
| Zeaxantin | 5 mg. |

| Formula n. 22 as Immune Booster | |
|---|---|
| Vitamin C | 500 mg. |
| Vitamin E | 400 I.U. |
| L-glutathione | 200 mg. |
| Selenium | 50 mcg. |
| Coenzyme $Q_{10}$ | 100 mg. |
| Green Tea Extract | 100 mg. |
| Melatonin | 5 mg. |

| Formula n. 23 for alcohol abuse | |
|---|---|
| Vitamin A | 10,000 I.U. |
| Vitamin D | 400 I.U. |
| Vitamin E | 100 I.U. |
| Vitamin K | 500 mcg. |
| Vitamin C | 500 mg. |
| Vitamin $B_1$ (thiamine) | 15 mg. |
| Vitamin $B_2$ (riboflavin) | 5 mg. |
| Vitamin $B_3$ (niacin) | 200 mg. |
| Vitamin $B_6$ | 5 mg. |
| Vitamin $B_{12}$ (cobalamin) | 3 mcg. |
| Folacin | 400 mcg. |
| Pantothenic acid | 50 mg. |
| Biotin | 200 mcg. |
| Zinc | 15 mg. |

| Formula n. 24 for alcoholic abuse | |
|---|---|
| Vitamin A | 10,000 I.U. |
| Vitamin E | 600 I.U. |
| Vitamin K | 10 mg. |
| Vitamin C | 10 mg. |
| Vitamin $B_1$ | 10 mg. |
| Vitamin $B_2$ | 50 mg. |
| Vitamin $B_3$ | 300 mg. |
| Vitamin $B_6$ | 50 mg. |
| Folacin | 4 mg. |
| Pantothenic acid | 50 mg. |
| Zinc | 15 mg. |

All of the above amounts are considered to be approximates or about amounts, and not necessarily an exact amount of each ingredient. Though the above formulas can also be provided in the exact amounts shown above and approximate, exact or about for all or some of the ingredients listed above are all considered within the scope of the invention. The antioxidants object of this invention have been carefully selected and tested by the best laboratories and universities, and their compositions guarantee the highest effectiveness in improving the immune system and in scavenging free radicals. The above mentioned antioxidants as nutritional support formulation helps to restore essential nutrients that may be lost or drained away by certain or by pollution or as free radicals scavenger. The formulas provide other key vitamins and minerals that work together to help the body metabolized the depleted nutritional ingredients that are essential to maintain good health.

While the invention has been described and disclosed in certain terms and has been illustrated by disclosure of certain embodiments or modifications persons skilled in the art who have acquainted themselves with the inventions will appreciate that it is not necessarily limited by such terms nor to the scientific or specific embodiments and modifications disclosed herein. Thus, a wide variety of alternatives suggested by the teachings herein, can be practiced without departing from the spirit of the invention, and rights to such alternatives are particularly reserved, especially those, which fall within the scope of appended claims.

What is claimed is:

1. A method for determining oxidative stress in a subject comprising:
   a) blending a sample of urine from a subject with a solution which contains methylene blue and at least one chromogen suitable for reacting with malondialdehyde to produce a visually detectable colorimetric change; and
   b) detecting the colorimetric changes in the blended urine; wherein a reddish colorimetric change is indicative of the presence of oxidative stress.

2. A method of claim 1 wherein the detection occurs at least about 15 to 20 minutes after blending the sample.

3. A method of claim 1, wherein the at least one chromogen comprises 1,3-diethyl-thiobarbituric acid.

4. A method of claim 3 wherein the detection occurs at least about 15 to 20 minutes after blending the sample.

5. A method of claim 1, wherein the at least one chromogen comprises 1,3-Diethyl-thiobarbituric Acid and pararosaniline sulphate.

6. A method of claim 5 wherein the detection occurs at least about 15 to 20 minutes after blending the sample.

7. A method of claim 1, wherein the at least one chromogen comprises 1,3-Diethyl-thiobarbituric Acid and 1,2-dimethylindole.

8. A method of claim 7 wherein the detection occurs at least about 15 to 20 minutes after blending the sample.

9. A method of claim 1 wherein the at least one chromogen comprises pararosaniline sulphate.

10. A method of claim 9 wherein the detection occurs at least about 15 to 20 minutes after blending the sample.

11. A method of claim 1 wherein the at least one chromogen comprises 1,2-dimethylindole.

12. A method of claim 11 wherein the detection occurs at least about 15 to 20 minutes after blending the sample.

13. A method of claim 1 wherein the at least one chromogen comprises 1,2-dimethylindole and pararosaniline sulphate.

14. A method of claim 13 wherein the detection occurs at least about 15 to 20 minutes after blending the sample.

15. A method of claim 1, wherein the chromogens are 1,3-diethyl-thiobarbituric acid, pararosaniline sulphate and 1,2-dimethylindole.

16. A method of claim 15 wherein the detection occurs at least about 15 to 20 minutes after blending the sample.

17. A method for determining oxidative stress in a subject comprising:
   a) blending a sample of urine from a subject with a solution which contains methylene blue and at least two chromogens suitable for reacting with malondialdehyde to produce a visually detectable colorimetric change; and
   b) detecting the colorimetric changes in the blended urine; wherein a reddish colorimetric change is indicative of the presence of oxidative stress.

18. A method of claim 17 wherein the detection occurs at least about 15 to 20 minutes after blending the sample.

\* \* \* \* \*